United States Patent [19]

Saifer et al.

[11] 4,022,224

[45] May 10, 1977

[54] REDUCTION OF SUPEROXIDE ACCUMULATION CAUSED BY SMOKE INHALATION

[75] Inventors: Mark G. Saifer, Berkeley; Lewis D. Williams, Menlo Park; Wolfgang Huber, Atherton, all of Calif.

[73] Assignee: Diagnostic Data, Inc., Mountain View, Calif.

[22] Filed: Sept. 9, 1975

[21] Appl. No.: 611,662

[52] U.S. Cl. ............................ 131/262 R; 128/208
[51] Int. Cl.² ................. A24B 15/02; A61M 15/06
[58] Field of Search ............. 128/208; 131/10.1, 9, 131/261 R, 261 A, 262 R, 262 A, 262 B; 424/177, 112, 101; 260/112

[56] References Cited

FOREIGN PATENTS OR APPLICATIONS 1,204,018  9/1970  United Kingdom .............. 131/10.1

OTHER PUBLICATIONS

"Tobacco & Tobacco Smoke", Wynder et al., 1967 Academic Press, New York & London, pp. 461–464 cited.
"Superoxide Dismutase", McCord et al., The Journal of Biol. Chem., vol. 244, No. 22, pp. 6049–6055 cited, issue 11/25/1969.

*Primary Examiner*—Robert W. Michell
*Assistant Examiner*—V. Millin
*Attorney, Agent, or Firm*—Millen & White

[57] ABSTRACT

The toxic effects of smoke inhalation are reduced by the inhalation of an amount of orgotein effective to reduce the amount of superoxide radicals produced in the respiratory tract by the smoke.

8 Claims, No Drawings

REDUCTION OF SUPEROXIDE ACCUMULATION CAUSED BY SMOKE INHALATION

BACKGROUND OF THE INVENTION

This invention relates to the use of orgotein to reduce the adverse effects of smoke inhalation.

Orgotein is the non-proprietary name assigned by the United States Adopted Name Council to members of a family or water-soluble protein congeners in drug form, i.e., the substantially pure injectable protein, substantially free from other proteins which are admixed or associated therewith. U.S. Pat. No. 3,758,682 claims pharmaceutical compositions comprising orgotein. Various uses of orgotein are claimed in U.S. Pat. Nos. 3,637,441; 3,773,928; 3,773,929 and 3,781,414.

In 1969 the bovine congener of the orgotein protein was discovered to be an enzyme which has the ability to catalyze the destruction of superoxide radicals via disproportionation into molecular oxygen and hydrogen peroxide. The name, superoxide dismutase (SOD), was assigned to the protein on the basis of this enzyme activity. McCord, J. M. and Fridovich, I. (1969) J. Biol. Chem. 244, 6049–6055.

The superoxide radical is a toxic product of oxygen-based metabolism. SOD is a natural endocellular defense mechanism against such toxicity. Misra, H. P. and Fridovich, I., (1972) J. Biol. Chem. 247, 3170–3175; Fridovich, I., Advan. Enzymol. 41, 35–97 (1975).

Because naturally occurring orgotein is present endocellularly in the body, its function ordinarily is limited totally or primarily to the endocellular environment. When orgotein is administred topically or systemically, its activity is manifested exocellularly, thus producing physiological effects not manifested or manifested to a lesser degree by the patient's naturally occurring SOD.

It has long been known that the inhalation of smoke, whether by smoking tobacco or by the inhalation of smoke present in the air, produces toxic effects in mammals. See Leuchtenberger et al., Nature, Vol. 247, No. 5442, pp. 565–567, (1974), and cases cited therein. In the cases of heavy smoke inhalation, whether through excess tobacco smoking or breathing air having a high concentration of smoke particles therein, the toxic effects manifest themselves in a variety of ways, sometimes dramatically and acutely. Also, the inhalation of smoke particles at sub-acute toxic levels over long periods of time produces irreversible pathological changes in the lung tissues.

H. H. Seliger et al., Science 1974, 185: 253–256, reported that cigarette smoke contains high concentrations of unstable molecules that react with oxygen to produce chemiluminescense.

It is an object of this invention to provide methods for reducing the toxic effects of smoke inhalation. Other objects will be apparent to those skilled in the art.

SUMMARY OF THE INVENTION

According to this invention, the toxic effects of smoke inhalation are reduced by the administration by inhalation proximate the time of smoke inhalation of an amount of orgotein effective to reduce substantially the concentration of superoxide radicals generated in the respiratory tract by the smoke.

DETAILED DISCUSSION

The present invention is based upon the discovery that smoke particles, in the presence of oxygen and moisture, produce copious amounts of superoxide radicals and that orgotein administered by inhalation suppresses the concentration of those radicals and ameliorates the toxic effects of smoke inhalation.

In preferred aspects of this invention, a. orgotein is administered in the form of an aerosol, either as liquid or solid particles;

b. orgotein is administered concurrently during the period of smoke inhalation;

c. orgotein is administered prior to or promptly after the inhalation of the smoke, preferably prior thereto; and d. orgotein is administered to a human, preferably when the inhaled smoke is tobacco smoke.

Although this invention is directed preferably to reducing the toxic effects of the inhalation of tobacco smoke, it will be apparent the method is also useful to reduce the toxic effects of inhaling other types of smoke, e.g., from industrial emission, forest fires and burning structures.

The orgotein is administered proximate the period of smoke inhalation, preferably within a few minutes, e.g., up to 60 minutes, or concurrently therewith, e.g., inhaled intermittently with the inhalation of the smoke. However, because the production of superoxide radicals persists for several hours and because at least a portion of the toxic effects of smoke inhalation are systemic in character, the orgotein is effective to ameliorate these toxic effects if administered up to about 6 hours beforehand or after.

The orgotein is normally administered by inhalation, preferably as an aerosol. It can be administered in an aerosol as an aqueous solution or as a micronized powder, either alone or in admixture with an inert physiologically acceptable solid carrier, preferably sucrose. See U.S. Pat. No. 3,637,640.

The total amount of orgotein administered is about 4 to 25 mg., preferably 8–12 mg. the upper limits of these ranges preferably in several separate doses and the lower limits as one or several separate dosages. Administration of this amount can be repeated, e.g., every 4–12 hours or so. Particularly when the inhalation of smoke is prolonged, a larger plurality of smaller doses, e.g., 0.1 – 0.5 mg. per dose, is preferred.

The production of superoxide radical and the inhibition thereof with orgotein during the interaction of cigarette smoke with aqueous solutions in air was investigated experimentally in vitro by following spectrophotometrically the reduction and oxidation of cytochrome C at pH 7.4 in the presence and absence of SOD. An initial non-inhibitable reduction is superimposed on a slow reaction which seems to produce both superoxide (which is inhibited by superoxide dismutase) and some species capable of oxidizing ferrocytochrome C.

The effect of cigarette smoke in the reduction of cytochrome C is complex, but orgotein partially inhibits the reaction, thus establishing definitely that the superoxide radical is produced during the interaction of smoke, water and air.

In the experiments, tobacco smoke from king size cigarettes (Raleigh Filter Kings with the filter intact or more often cut off) was obtained with a 35 cc disposable syringe. Two 35 cc puffs were drawn and expelled.

Then the required amount of smoke is either drawn into a clean syringe containing 1 or 2 ml. of buffer, cytochrome C mix, or dimethylformamide (DMF) and shaken vigorously for 30 seconds, or else filtered through a 2.4 cm Whatman GF/C or GF/D glass fiber filter on a Swinnex holder. The filtered particles were extracted from the filter by swirling for a few minutes in a beaker with 2 ml. DMF and decanting.

All procedures were carried out under ambient light (fluorescent). Cytochrome C mix consisted of $10^{-4}$ M ethylenediamine tetraacetic acid (EDTA) + $10^{+5}$ M cyctochrome C (Sigma type III from horse heart) in 0.067 M pH 7.4 phosphate buffer 0.45% NaCl. Some experiments were run at pH 10.2 in 0.05 M carbonate buffer at the same EDTA and cytochrome C concentrations. The orgotein was isolated from beef liver (3,300 units/mg.).

The rate of reduction of cytochrome C was measured at room temperature at the 550 nm absorbance maximum of ferrocytochrome C with a Gilford 240 UV-VIS spectrophotometer. The absorbance increase for the reduction was taken to be $2.1 \times 10^4$ $M^{-1}$ $cm^{-1}$. The start of reaction was taken as the time shaking of smoke and aqueous solution was started, or at the time the DMF extract was added to the aqueous solution.

The results of these experiments are:

1. Addition of cigarette smoke to cytochrome C mix at either pH 7.4 or pH 10.2 leads to an increase in absorbance at 550 nm over a period of minutes to hours. The method of adding the smoke, either directly or as a DMF extract, made a quantitative, but not a qualitative, difference in the rate and extent of the OD increase. Pre-solution of smoke in DMF give more reaction per volume of smoke.

2. The spectral changes at 550 nm appear to be due chiefly to oxidation and reduction of cytochrome C, but with interference by suspended solids due to the insolubility of smoke in water. Addition of smoke directly to buffer in the absence of cytochrome C caused no optical density increase with time at pH 7.4 and only a minor increase with time at pH 10.2, but the solutions were hazy. Addition of smoke in DMF gave an initially clear solution which gradually grew opalescent with a corresponding increase in OD. Filtration through a 3 $\mu$ Millipore filter reduced the OD's to values consistent with the cytochrome C concentration. Reduction of the filtered solutions with excess sodium dithionite gave OD's essentially the same (8% range) regardless of the amount of smoke added originally, thereby indicating that there were no irreversible changes preventing reduction of ferrocytochrome C involved in the OD changes measured.

3. Orgotein, whether present from the beginning or added at later times, reduced the rate of $OD^{550}$ increase below that of a similar solution without orgotein. This difference in rate (which should correspond to the rate of superoxide production) is fairly constant for a relatively long time at lower smoke concentrations. For example, at 0.18 cc smoke/ml cytochrome C mix, the rate decrease in the presence or orgotein amounted to 0.088 $OD^{260}$ /min. or $d(O_2^-)/dt = 1.6 \times 10^{-9}$ M $min^{-1}$ for over 4 hours. Moreover, the rate of superoxide production appears to be proportional to the smoke concentration, at least at low smoke concentrations.

4. The initial, more rapid reduction was not inhibited by orgotein. For the 0.18 cc smoke/ml cytochrome C mix solution, this initial reduction amounted to 0.06 OD ($2.9 \times 10^{-7}$ M) and was over within 1½ hours.

5. The leveling off of the OD increase after several hours at moderate to high concentrations of smoke and in the absence of orgotein represents a dynamic oxidation-reduction equilibrium rather than a cessation of reaction. Addition of orgotein shifts this equilibrium to the oxidizing side by removing the cytochrome C reductant (superoxide) with a corresponding OD decrease following the initial non-inhibitable increase mentioned above.

6. The dependence of inhibition on SOD concentration appears to correspond to 50% inhibition at about 0.2 – 0.3 $\mu$ g/ml orgotein at pH 7.4, with little further inhibition above 2 $\mu$ g/ml orgotein. This is similar to the concentration dependence of inhibition when a known superoxide source such as xanthine-xanthine oxidase, is used at pH 7.4, $10^{-5}$ M cytochrome C, and indicates that superoxide is not a required chain-carrying radical for the reactions involved in its production in the smoke-water system.

7. Comparison of the smoke particulate matter with the filtered gas showed that 80–90% of the cytochrome C reduction capacity of the smoke in the absence of orgotein is in the particulate matter.

8. The presence of the cigarette filter reduced the initial OD increase somewhat, but had no definite effect on the orgotein-inhibitable reaction.

The pharmaceutical compositions of this invention comprise an effective amount of orgotein in admixture with a pharmaceutically acceptable carrier, i.e., orgotein is present therein in a unit dosage amount of orgotein effective to ameliorate the toxic effects of smoke inhalation upon inhalation of an effective dose of the pharmaceutical composition, either as a single or in divided doses. Although the most effective mode of administration for ameliorating the toxic effects of smoke inhalation is by inhalation of the orgotein-containing pharmaceutical composition, at least a portion of the toxic effects of smoke inhalation ameliorated by inhalation of orgotein can also be ameliorated by parenteral administration, e.g., I.M. Therefore, such alternative mode of administration is a contemplated, albeit less preferred, equivalent of the preferred mode of inhalation administration.

In our prior-filed application Ser. No. 207,685, filed September 20, 1974, now abandoned, and in our applications, Ser. No. 611,657, filed Sept. 9, 1975; Ser. No. 611,658, filed Sept. 9, 1975; and Ser. No. 611,659, filed Sept. 9, 1975, now U.S. Pat. No. 4,009,267; filed on even date herewith, whose disclosures are incorporated herein by reference, are disclosed derivatives of orgotein which, like orgotein, possess both SOD and anti-inflammatory activity. Such derivatives are contemplated functional equivalents or orgotein in the process of this invention.

For examples of devices for administering liquid and solid aerosols, see, e.g., U.S. Pat. Nos. 3,732,864; 3,560,607; 3,456,646; 3,456,645; 3,456,644; 3,302,834; 3,187,748; 3,157,179; and 3,001,524.

Without further elaboration, it is believed that one skilled in the art can, using the preceding description, utilize the present invention to its fullest extent. The following preferred specific embodiments are, therefore, to be constructed as merely illustrative and not limitative of the remainder of the disclosure in any way whatsoever.

PREPARATION 1

A finely divided powdered sterile mixture of substantially pure orgotein is dissolved in sterile water or buffer (pH 7.5) to provide a sterile 1% SOD solution and mixed with an amount of an inert propellant conventionally employed for oral inhalation compositions and packaged in a nebulizer ("Devilbis") so as to dispense with each discharge of the nebulizer a measured dose of about 0.025 cc. (0.25 mg. orgotein) of the solution with an average particle size of less than 5 microns and preferably not less than 0.5 microns.

PREPARATION 2

Prepare the following composition:

| | Percent |
|---|---|
| Orgotein and sucrose mixture (1:2 ratio, particle size 2–8 microns) | 0.1 |
| Sodium dioctylsulfosuccinate | 0.002 |
| Dichlorotetrafluoroethane | 30–40 |
| Dichlorodifluoromethane | 70–60 |

Incorporate the foregoing in a pressurized aerosol dispensing package, e.g., as disclosed in U.S. Pat. Nos. 3,302,834 or 3,732,864.

Similarly, solid and solution formulations suitable for inhalation can be prepared with sucrose in a weight ratio to SOD of about 2:1.

PREPARATION 3

Blend lyophilized orgotein with micronized lactose crystals at 1 to 3 mg lactose per 1 mg protein, dispense into gellatine capsules at the desired unit dose rate and administer by inhalation through a turbo-inhaler (Spinhaler Fisons Corporation).

EXAMPLE 1

A few seconds to 1-2 minutes prior to smoking a cigarette, the smoker inhales an aerosol of 0.25 mg. or substantially pure orgotein (1,800 – 3,300 SOD units/mg.) from a dispenser according to Preparation 1 or 2. Inhalation is repeated, preferably prior to or during smoking, until about 1 to 10 mg. of SOD is inhaled.

EXAMPLE 2

Within about one hour prior to or after entering an area having a high concentration of smoke, such as a burning building, field or forest, the persons who are to be or have been exposed to the smoke, inhale orgotein in the manner described in Example 1. The number of further inhaled dosages of the SOD should be increased if the period of exposure is prolonged.

EXAMPLE 3

The procedure of Example 2 is followed plus an 8 mg. dose of a sterile solution of 8 mg. orgotein and 16 mg. of sucrose is administered intramuscularly from 0.25 to 2 hours prior to exposure to the smoke.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A method for reducing the toxic effects of smoke inhalation by a mammal which comprises administering thereto by inhalation, proximate the inhalation of the smoke, of an amount of orgotein effective to reduce the concentration of superoxide radicals generated by the smoke in the respiratory tract of the mammal.

2. A method according to claim 1, wherein the orgotein is administered as an aerosol.

3. A method according to claim 1, wherein the orgotein is administered to a human being.

4. A method according to claim 3, wherein the smoke is tobacco smoke.

5. A method according to claim 1, wherein the orgotein is administered in admixture with the smoke.

6. A method according to claim 5, wherein the orgotein is administered as an aerosol to a human being and the smoke is tobacco smoke.

7. A method according to claim 1, wherein the orgotein is administered prior to inhalation of the smoke.

8. A method according to claim 2, wherein the orgotein is administered as an aerosol to a human being and the smoke is tobacco smoke.

* * * * *